United States Patent [19]

Silver et al.

[11] 4,153,056

[45] May 8, 1979

[54] SYRINGE WITH REMOVABLE LENGTH ADJUSTING MEMBER

[75] Inventors: Jules Silver, 166 Yantic St., Norwich, Conn. 06360; Jerome Silverstein, North Franklin,, Conn.

[73] Assignee: Jules Silver, Norwich, Conn.

[21] Appl. No.: 807,317

[22] Filed: Jun. 16, 1977

[51] Int. Cl.² ............................................. A61M 1/00
[52] U.S. Cl. ................................. 128/234; 128/218 C
[58] Field of Search ......... 128/218 R, 218 P, 218 PA, 128/218 C, 234, 215; 141/27; 222/309

[56] References Cited

U.S. PATENT DOCUMENTS

| | | | |
|---|---|---|---|
| 1,569,457 | 1/1926 | Carstens | 128/218 C |
| 1,948,982 | 2/1934 | Cutter | 128/218 P |
| 2,002,024 | 5/1935 | Wood | 128/218 PA |
| 3,237,660 | 3/1966 | Hill | 128/218 C |
| 3,770,026 | 11/1973 | Isenberg | 141/27 X |
| 3,934,586 | 1/1976 | Easton et al. | 128/218 C |
| 4,073,321 | 2/1978 | Moskowitz | 141/27 |

FOREIGN PATENT DOCUMENTS 1212823 11/1970 United Kingdom ............... 128/218 C Primary Examiner—John D. Yasko

[57] ABSTRACT

A syringe for dispensing medicaments or other materials includes a hollow syringe body having a discharge end portion and an open opposite end portion through which a plunger is slidably received. The plunger has a first end portion located within the syringe body and includes an integral seal forming a seal between the plunger and the interior of the syringe body. A removable length adjusting member is threadably engaged on the plunged outside of the syringe body to variably limit operating travel of the plunger in the syringe body, thereby to control the amount of material in the syringe body expelled therefrom upon depression of the plunger into the syringe body.

11 Claims, 4 Drawing Figures

U.S. Patent    May 8, 1979    4,153,056
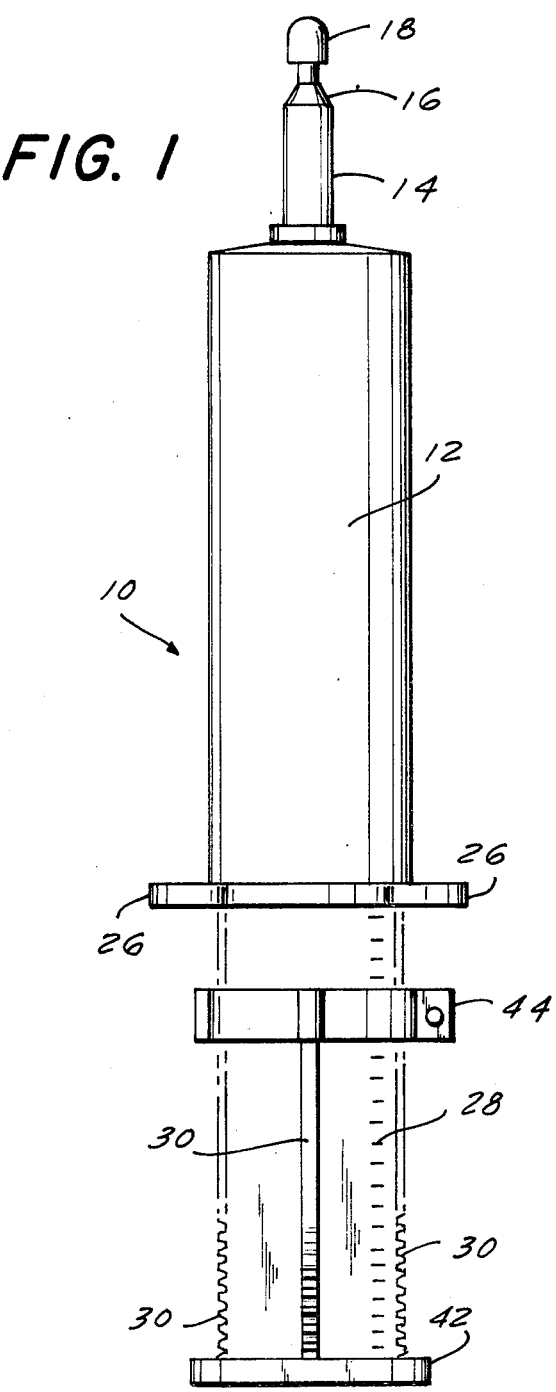
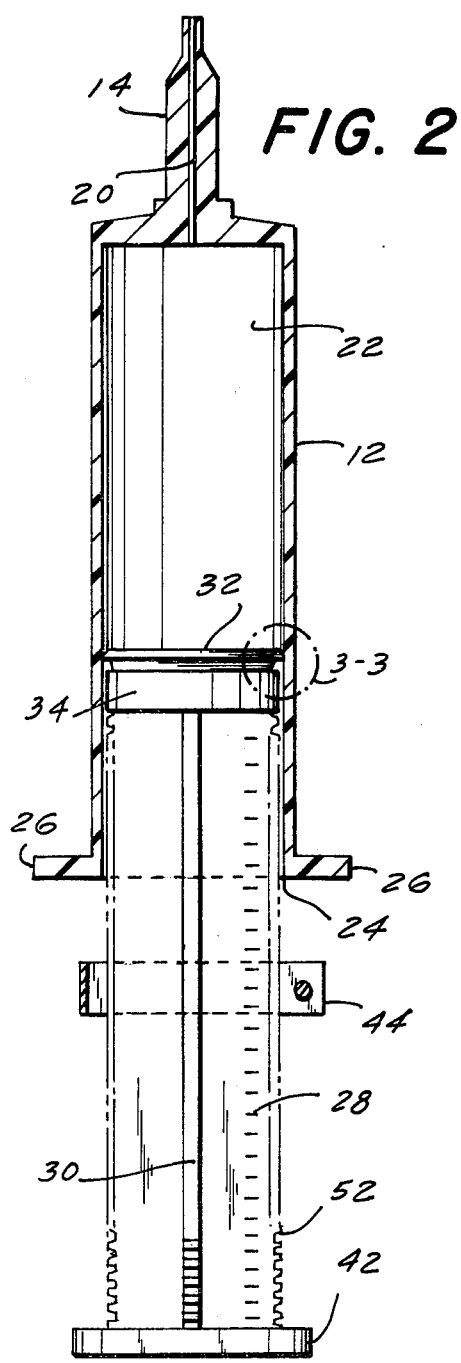
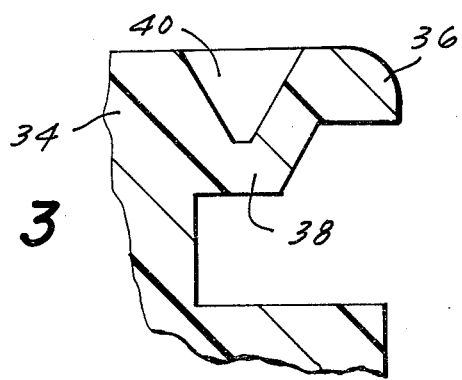
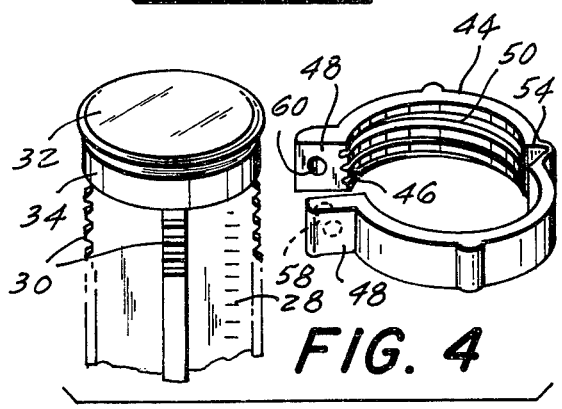

SYRINGE WITH REMOVABLE LENGTH ADJUSTING MEMBER

The present invention relates to syringes, and in particular to a syringe structure which is adapted to dispense measured quantities of material contained within the syringe.

Previously proposed syringe structures, such as disclosed in U.S. Pat. No. 3,563,240 have been used, particularly in the veterinary field, to dispense measured doses of a medicament in the syringe. Syringes of this type are provided with a plunger having means defining peripheral threads on which a threaded nut or the like is mounted. By adjusting the position of the nut along the length of the plunger the operating travel of the plunger in the syringe body is limited upon depression of the plunger by the nut when it is engaged against the end of the syringe body.

In the manufacture of such previously proposed syringe structures, the plunger is formed of a molded plastic construction such that its maximum external diameter is smaller than the internal diameter of the syringe in which it is to be used. The threaded nut is then threadably engaged on the plunger over the inner or piston end thereof. After the nut is in position, a flexible rubber seal or the like is mounted on the inner end of the plunger in order to form a seal with the interior of the syringe body when the plunger is placed in the syringe chamber after the syringe is filled with the desired medicament. Because it is necessary to threadably engage the nut on the plunger stem, no portion of the inner end of the plunger stem can have diameter greater than the internal diameter of the threads formed on that stem, otherwise there would be interference with the nut which would prevent the nut from being threadably engaged with the plunger stem. Therefore with syringes of the type described in U.S. Pat. No. 3,563,240 it is not possible to provide an integral seal on the inner end of the plunger, since the seal must have an external diameter which is greater than the internal diameter of the syringe, in order to form a proper seal with the internal wall of the syringe chamber. Thus it is mandatory that a separate flexible seal be mounted on the end of the plunger, after the nut is in place, in order to provide the desired seal at the piston end of the plunger. As a result, the cost involved in manufacturing syringes of this type is greatly increased since additional operations are required in placing the flexible seal on the inner end of the plunger and additional materials are required. Moreover, with such previously proposed syringes, in order to vary the dosage to be applied with the syringe to a great extent it is necessary to rotate the nut through a relatively large distance, and this is a time consuming operation.

It is an object of the present invention to provide a syringe structure having an adjustable dosage feature, but which uses an integral seal formed integrally with the plunger element.

Another object of the present invention is to provide a variable dosage syringe in which the element controlling the variation in dosage can be rapidly moved from one position to another along the length of the plunger stem.

Another object of the present invention is to provide a variable dosage syringe which is relatively inexpensive to manufacture.

Another object of the present invention it to provide a variable dosage syringe which is relatively simple to manufacture and durable in use.

In accordance with an aspect of the present invention the syringe includes a hollow syringe body having a discharge end portion and an open opposite end portion. The hollow syringe body defines a chamber therein which is adapted to contain a material, such as for example a veterinary medicament, to be dispensed through the discharge end portion of the syringe. A plunger is slidably received in the chamber of the syringe through the open end portion of the body. The plunger has first and second opposite end portions with the first end portion thereof located in the syringe chamber and having a transverse piston formed thereon. The piston includes a main body portion and an integral peripheral flange whose peripheral configuration is generally complementary to the internal configuration of the syringe chamber, thereby to form a seal against the inner surfaces of the syringe body. An integral flexible peripheral web connects the flange to the main body portion of the piston.

Integral seals of this type for use on plunger devices are known, but such integral seal arrangements cannot be used with syringes of the type disclosed in U.S. Pat. No. 3,563,240 since the diameter of the sealing flange must be greater than the maximum dimensions of the stem of the plunger in order to form an adequate seal. Since the internal opening in the threaded nut used with threaded plungers of the type disclosed in the above mentioned patent is somewhat smaller than the maximum dimensions of the stem, i.e. the diameter between the inner edges of the threads of the nut is less than the maximum diameter of the plunger, since the threads are inserted in the grooves on the plunger, the nut could not fit over this type of seal element.

In the present invention a removable length adjusting member or nut is threadably engaged with the threaded stem of the plunger outside of the syringe body and includes means for releasing the engagement of the length adjusting member to permit removal thereof from the plunger laterally of the longitudinal axis thereof. In one embodiment, the removable length adjusting member can be a one piece hinged element having two adjacent open end portions which can be releasably secured to each other to form a complete annular nut. When it is desired to place the nut on the stem of the plunger, all that is necessary is to open the end portions of the nut, spread the ends apart, and insert the plunger therebetween. Thereafter the nut can be closed about the plunger stem and the ends thereof lock together to form the complete nut. By this construction a variable dosage syringe can be provided which also has the desirable integral seal plunger formed thereon. Moreover, the nut can be readily removed and replaced by the user of the syringe at varying positions along the stem, to more rapidly adjust the dosage to be supplied with the syringe, without the need for threadably moving the nut from one position to another.

The above, and other objects, features and advantages of this invention will be apparent in the following detailed description of an illustrative embodiment thereof, which is to be read in connection with the accompanying drawings, wherein:

FIG. 1 is an elevational view of a variable dosage syringe constructed in accordance with more embodiment of the present invention;

FIG. 2 is a longitudinal sectional view of the syringe shown in FIG. 1;

FIG. 3 is an enlarged partial sectional view of an edge portion of the plunger piston and seal arrangement of the present invention; and FIG. 4 is a partial exploded perspective view illustrating the openable nut of the present invention in relation to the threaded stem of the plunger.

Referring now to the drawing in detail and initially to FIG. 1 thereof, a variable dosage syringe 10 includes a hollow syringe body 12 formed of a synthetic plastic material or the like which includes an elongated tubular cannula 14 having a tapered end portion 16 that is selectively closed by a removable ap 18. As seen in FIG. 2, cannula 14 has a bore 20 formed therein which communicates with the internal chamber 22 of syringe body 12. This chamber is adapted to receive a pharmaceutical preparation or the like which is intended to be dispensed from chamber 22 through bore 20 of cananula 14.

Chamber 22 has a uniform diameter from one end to the other and is open at the end 24 thereof opposite cannula 14. Laterally extending handles or finger flanges 26 are provided adjacent this end of syringe body 12, in the conventional manner.

The medicament is expelled from the chamber 22 through bore 20 by a plunger 28 which consists of an integral body formed of a plurality of radially extending flat flanges 30 in a cruciform array. The plunger has a first or inner end portion 32 which includes an integral piston 34 formed thereon adapted to be inserted through open end 24 of syringe body 12. The opposite end of plunger 28 has an integral palm or thumb engaging base or flange 42 formed thereon in the conventional manner.

Piston 34 includes an integral annular flange 36 surrounding the piston and having a diameter which is greater than the maximum diameter of the stem portion 28 of the plunger. As seen in FIG. 3 flange 36 is connected to piston 34 by an integral annular web 38 which is formed in the piston by an annular V-shaped notch 40, so that web 38 has a reduced thickness as compared to flange 36 and is flexible, to permit the flange to serve as a wiping seal along the interior surface of syringe body 12.

A plunger limiting nut or ring 44 is provided which is adapted to be removed from the plunger, without passing the end 32 thereof. In the illustrative embodiment of the invention rng 44 is formed as a one-piece generally annular element having a slot or slit 46 formed therein to define two free end portions 48. The internal surface 50 of the ring is threaded to threadably engage the notches 52 formed in outer edges of plunger flanges 30. These notches form a continuous thread on the plunger, so that ring 44 can be threaded along the length thereof.

Ring 44 is also provided with an integral flange 54, located diametrically opposite split 46 in the ring. Hinge 54, which comprises a thin plastic V-shaped section, permits the ends 48 of the ring to be spread apart, to open split 46 so that plunger 28 can be laterally inserted into the confines of ring 44. After the plunger is positioned ends 48 are moved towards each other, to close the ring. The ring is held in this closed position by a stud 58 on one of the ends 48 of the ring which is frictionally received in an opening 60 in the other ring end 48. With the ring in its closed position, locked by the frictional engagement of stud 58 and opening 60, the threads on the internal surface of the ring form a continuous threaded path.

With ring 44 on plunger 28, the ring can be rotated to be properly located along the length of the plunger so as to permit a proper dosage of the material in the chamber to be expelled through cannula 14. Thus, by adjusting the distance of annular ring 44 from finger flanges 26 on the cannula, more or less material from the syringe can be expelled. In addition, when a large adjustment in the dosage is necessary, rather than rotating ring 44 along the entire length of the plunger the ring is simply opened by the operator, by separating the ends 48 thereof, removing the ring form the plunger, and replacing it on the plunger down closer to its base 42. Thus the operator can far more rapidly make large adjustments in dosage applications than was heretofore possible. In this regard, it is noted that the ring adjustment arangement of the invention is not limited to the use of a thread-type series of notches the plunger. For example, where the fine adjustment permitted by the thread arrangement is not needed the plunger can simply to provided with spaced notches into which the ring may be snapped. Alternatively the ring and plunger can be arranged to have a tight frictional fit and engagement. Also, the ring 44 can be made from two separate semi-circular members each having a stud 58 and opening 60 at their opposite ends to be completely separable.

Accordingly it is seen that by the present invention ring 44 enables plunger 28 to be provided with an integral and inexpensive seal arrangement that could not be used in previously proposed variable syringe devices wherein a rigid solid non-removable rotating nut is used. In addition, the ring enables the dosage to be supplied by the syringe to be rapidly changed, by permitting rapid movement of ring 44 from one position to another along the plunger shaft.

Although an illustrative embodiment of the present invention has been described herein with reference to the accompanying drawings, it is to be understood that the invention is not limited to that precise embodiment, and that various changes and modifications may be effected therein by one skilled in the art without departing from the scope or spirit of this invention.

What is claimed is:

1. A syringe comprising a hollow syringe body having a discharge end portion and an open oposite end portion, a plunger slidably received in said syringe body through said open end portions thereof, said plunger having a first end portion located within said syringe body including a seal formed thereon forming a seal between the plunger and the interior of the syringe body; and a removable length adjusting member engaged with said plunger outside of the syringe body to variably limit operating travel of the plunger in the syringe body thereby to control the amount of material in the syringe body expelled therefrom upon depression of the plunger into the syringe body; said removable length adjusting member comprising an internally threaded nut including at least two adjacent separable edge portions and means for selectively securing said edge portions together.

2. A syringe as defined in claim 1 wherein said removable length adjusting member comprises a one piece collar having an internal thread formed thereon, said collar being split in at least one location along its periphery to define two adjacent separable edge portions permitting the collar to be opened to allow lateral placement or removal of the collar onto the plunger.

3. A syringe as defined in claim 2 wherein said collar includes an integral flexible hinge formed therein diametrically opposite to said split.

4. A syringe as defined in claim 1 wherein said intgeral seal comprises an annular flange formed in said first end portion of the plunger having a diameter greater than the diameter of adjacent portions of the plunger and an integral flexible annular web connecting said flange to said plunger.

5. A syringe comprising a hollow syringe body having a discharge end portion and a open opposite end portion and defining a chamber therein adapted to contain a material to be dispensed through said discharge end portion; a plunger slidably received in said chamber through said open end portion of the syringe body, said plunger having first and second opposite end portions with said first end portion located in said chamber and having a transverse piston formed thereon, said piston including a main body portion, an integral peripheral flange whose peripheral configuration is generally complementary to the internal configuration of said chamber to form a seal against the inner surface of the syringe body and an integral flexible peripheral web connecting said flange to said main body portion; said plunger including a stem portion extending between said piston and said second plunger end portion having means thereon for defining a screw thread; and a removable length adjusting member threadably engaged with said stem of the plunger outside of the syringe body and including means for releasing the engagement of the length adjusting member to permit removal thereof from the plunger laterally of the longitudinal axis thereof; said removable length adjusting member comprising an internally threaded nut including at least two adjacent separable edge portions and means for selectively securing said edge portions together.

6. A syringe comprising a hollow syringe body having a discharge end portion and an open opposite end portion and defining a chamber therein adapted to contain a material to be dispsensed through said discharge end portion; a plunger slidably received in said chamber through said open end portion of the syringe body, said plunger having first and second opposite end portions with said first end portion located in said chamber and having a transverse piston formed thereon, said piston including a main body portion, an integral peripheral flange whose peripheral configuration is generally complementary to the internal configuration of said chamber to form a seal against the inner surface of the syringe body and an integral flexible peripheral web connecting said flange to said main body portion; said plunger including a stem portion extending between said piston and said second plunger end portion having means thereon for defining a screw thread; and a removable length adjusting member threadably engaged with said stem of the plunger outside of the syringe body and including means for releasing the engagement of the length adjusting member to permit removal thereof from the plunger laterally of the longitudinal axis thereof; said removable length adjusting member comprising a one piece collar having an internal thread formed thereon, said collar being split in at least one location along its periphery to define two adjacent separable edge portions permitting the collar to be opened to allow lateral placement or removal of the collar onto the plunger.

7. A syringe as defined in claim 6 wherein said collar includes a integral flexible hinge formed therein diametrically opposite to said split.

8. A syringe as defined in claim 7 wherein said syringe body is generally cylindrical and said flange is an annular flange.

9. A syringe comprising a hollow syringe body having discharge end portion and an open opposite end portion, a plunger slidably received in said syringe body through said open end portion thereof; and a removable length adjusting member engaged with said plunger outside of the syringe body to variably limit operating travel of the plunger in the syringe body, thereby to control the amount of material in the syringe body expelled therefrom upon depression of the plunger into the syringe body; said removable length adjusting member comprising an internally threaded nut including at least two adjacent separable edge portions and means for selectively securing said edge portions together.

10. A syringe comprising a hollow syringe body having a discharge end portion and a open opposite end portion, a plunger slidably received in said syringe body through said open end portion thereof; and a removable length adjusting member engaged with said plunger outside of the syringe body to variably limit operating travel of the plunger in the syringe body thereby to control the amount of material in the syringe body expelled therefrom upon depression of the plunger into the syringe body; said removable length adjusting member comprising a one piece collar having an internal thread formed thereon, said collar being split in at least one location along its periphery to define two adjacent separable edge portions permitting the collar to be opened to allow lateral placement or removal of the collar onto the plunger.

11. A syringe as defined in claim 10 wherein said collar includes an integral flexible hinge formed therein diametrically opposite to said split.

* * * * *